United States Patent [19]
Heyden et al.

[11] 4,087,398
[45] May 2, 1978

[54] ANTIFOAM COMPOSITIONS

[75] Inventors: Rudi Heyden, Erkrath; Adolf Asbeck; Michael Eckelt, both of Dusseldorf, all of Germany

[73] Assignee: Henkel Kommanditgesellschaft auf Aktien (Henkel KGaA), Dusseldorf-Holthausen, Germany

[21] Appl. No.: 745,839

[22] Filed: Nov. 29, 1976

[30] Foreign Application Priority Data

Dec. 1, 1975 Germany .............................. 2553990

[51] Int. Cl.$^2$ ................................................ C08L 33/08
[52] U.S. Cl. ........................ 260/29.6 R; 260/29.6 RB; 260/29.6 RW; 252/321; 252/358; 260/593 R; 568/840
[58] Field of Search .............................. 252/321, 358; 260/632 R, 593 R, 29 R

[56] References Cited

U.S. PATENT DOCUMENTS

| | | | |
|---|---|---|---|
| 2,363,922 | 11/1944 | Denman | 252/321 |
| 2,715,613 | 8/1955 | Gibson | 252/321 |
| 3,267,180 | 8/1966 | Ayres et al. | 260/880 R |
| 3,781,428 | 12/1973 | Hennart et al. | 239/60 X |
| 4,009,119 | 2/1977 | Poschmann et al. | 252/321 |

OTHER PUBLICATIONS

Struve et al., Chemical Abstracts 81 (1974), 79693g.

*Primary Examiner*—Benjamin R. Padgett
*Assistant Examiner*—E. Suzanne Parr
*Attorney, Agent, or Firm*—Hammond & Littell

[57] ABSTRACT

Liquid dispersions of the higher ($C_{22-70}$) aliphatic ketones and higher ($C_{22-70}$) aliphatic secondary alcohols are effective antifoaming agents when they are of fine particle size. The particle size should be at least sufficiently small that the dispersion does not substantially separate under normal storage conditions. The dispersed phase can be water or an organic liquid in which the dispersed phase is substantially insoluble. The dispersions are effective anti-foam agents for most industrial purposes, and are suitable for use in oil and latex paints.

36 Claims, No Drawings

ANTIFOAM COMPOSITIONS

FIELD OF THE INVENTION

The present invention relates to liquid compositions which are useful in decreasing the tendency of solutions, liquors and dispersions in a large number of industrial processes to form foam, and for breaking foam which has already formed. The invention includes methods for inhibiting the formation of foam and for breaking foam by the use of said liquid compositions. The invention is particularly directed towards oil and latex paints of decreased tendency to form foam when applied to surfaces in conventional manners.

BACKGROUND OF THE INVENTION

It is known that dispersions of certain solid materials in organic fluids or in water are effective antifoaming agents which are useful for defoaming industrial waste water and for inhibiting the formation of foam in paper-making white water, in the production of cellulose, in the production of dispersions of natural and synthetic film-forming materials (e.g. oil and latex paints) and pigment and dye dispersions, and in the manufacture of food. The antifoam agents referred to are finely divided solids of wax-like consistency, for example, pentaerythritol fatty acid esters, fatty acid monoglycerides, fatty acid polyglycol esters and the like (see U.S. Pat. No. 2,715,613).

OBJECTS OF THE INVENTION

It is a principal object of the invention to provide fluid anti-foaming compositions which are chemically- and storage- stable, and which can be used effectively in strongly acid and strongly alkaline media.

It is a further object of the invention to provide such compositions by use of comparatively readily available normally solid organic wax-like materials.

It is still a further object to provide organic and aqueous dispersions of film-forming materials (including latex paints) of decreased tendency to foam and which release foam quickly when applied to a shaped object including surfaces to be painted.

THE INVENTION

The present invention is based upon the discovery that liquid dispersions of certain normally solid long chain aliphatic ketones and certain normally solid long chain aliphatic secondary alcohols meet the objects stated above, provided that the ketone or alcohol is present in highly particulate form. The dispersions can be added advantageously to organic and aqueous compositions which have a tendency to foam under normal processing conditions (i.e., when agitated with inclusion of air). They are useful in breaking foam which has already formed.

In general, the invention is a dispersion wherein the continuous phase is a liquid having a solidification point below 5° C. and a boiling point above 80° C. and wherein the dispersed phase comprises at least 1%, based on the weight of the dispersion, of a higher aliphatic component selected from the group consisting of the $C_{22-70}$ aliphatic ketones, the $C_{22-70}$ aliphatic secondary alcohols and mixtures thereof, said continuous phase being substantially a non-solvent for said aliphatic component; the size of the particles of the dispersed phase being such that the dispersion does not separate on standing for two weeks at 20° C.; the amount of said dispersed phase being such that said dispersion is fluid at 40° C.

The compositions of the present invention consist essentially of a wax-like defoamer in an organic liquid or in water, characterised in that the defoamer is a ketone having a chain length of more than 22 carbon atoms or a secondary alcohol produced therefrom. The ketones or secondary alcohols referred to are wax-like substances and in pure state have well-defined melting points. If preferred, they may be mixtures of ketones of different chain length, or mixtures of alcohols of different chain length, or mixtures of the aforesaid ketones and alcohols in any proportions. Such mixtures melt over a more or less broad range.

The aforesaid ketones can be produced by known methods by catalytic removal of $CO_2$ and water from higher fatty acids having 12 or more chain carbon atoms according to the theoretical equation:

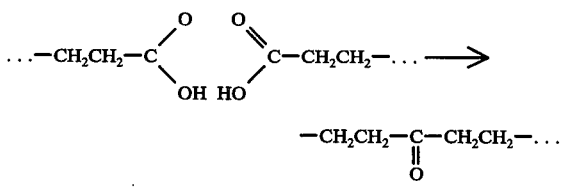

or by heating the calcium salts of the acids. The corresponding secondary alcohols are obtained by a hydrogenation of the ketones in the presence of a suitable catalyst. Ketones and alcohols of $C_{23}$ to $C_{43}$ are particularly suitable. Examples of ketones and alcohols within this range are:

| Name | Carbon Atoms In Chain | M.p. ° C. |
|---|---|---|
| 12-Tricosanone | | 70 |
| 12-Tricosanol | 23 | 75 |
| 14-Myristone | 27 | 76 |
| 16-Hentriacontanone (palmitone) | 31 | 84 |
| 16-Hentriacontanol | 31 | 85 |
| 18-Pentatriacontanone (stearone) | 35 | 88 |
| 18-Pentatriacontanol | 35 | 90 |

The aliphatic ketones and secondary aliphatic alcohols employed are compounds showing 22 to 60 carbon atoms selected from the group consisting of alkanones and secondary alkanols. Preferably compounds having from 22 to 50 carbon atoms are employed. The compounds prepared as above are symmetrical and have the ketone or secondary alcohol group in the middle of the chain.

The anti-foam component can be a mixture of the aforesaid ketones and alcohols in any proportion, and 50:50 molar mixture of the two gives good results and therefore is preferred.

The aliphatic chains of the ketones and secondary alcohols mentioned above may be branched, but the total number of carbon atoms in such branched chains should not be in excess of 70. The chains can contain one or more points of unsaturation, but we prefer that the chains be saturated because of their ease of production and the excellent results which they provide. The agents of the present invention thus can be alkanones and alkanols.

The liquid (continuous) phase of the dispersions of the present invention can be water or any other liquid in which the aforesaid ketones and alcohols are substantially insoluble which are liquid at normal room temperature, and which have a solidification point or melting point below 5° C. A high viscosity is also advantageous since this improves the storage-stability of the dispersions. The liquid phase itself may be a defoaming agent, or it may act only as a carrier for the defoamer. Suitable liquids for the purpose are materials which have boiling points above 70° C. (the melting point of tricosanone). These include esters of aliphatic acids (which may be branched and which may be unsaturated) having 8 to 18 carbon atoms with monovalent or polyvalent alcohols such as the glycol diester or glycerine triester of oleic acid and oleic oleate etc., and also branched chain saturated or unsaturated liquid fatty acids and fatty alcohols having 8 to 18 carbon atoms, for example isotridecyl alcohol and oleyl alcohol, and terpene hydrocarbons, for example pine oil, oil of turpentine and the like. However, preferable to all of these are mineral oils which have boiling points in excess of 140° C.

It is advantageous to use as the liquid (i.e., continuous) phase non-ionic hydrophobic (i.e., water-insoluble) organic fluids which at elevated temperature possess a good solvent power for the ketones or alcohols but which are substantial non-solvents for these materials at room temperature so that they precipitate the ketones and alcohols in finely divided form upon cooling. Liquids of this type render it possible to manufacture the defoaming dispersions in an economical manner by heating the solvent and the antifoam agents together and then rapidly cooling the resulting solution with intensive agitation, whereby an extremely fine-particulate and stable dispersion is obtained. Alternatively, however, it is possible to manufacture the dispersion by stirring the waxy antifoam agents in highly particulate form into the liquid phase at room temperature. The dispersions preferably contain approximately 5% to 15% by weight of the waxy antifoam agent, but may contain a larger or smaller proportion if desired, from 1% up to 100% by weight, as long as the dispersion is of fluid viscosity at normal temperature (20° C. - 40° C.). The liquid forming the continuous phase should have a boiling point sufficiently high (i.e., in excess of about 70° C.) to permit it to dissolve at least the lower members of the group of ketones and alcohols referred to above.

The invention depends in substanial part on the particle size of the dispersed ketone or alcohol (or ketonealcohol mixture). The particles should be sufficiently small so that the dispersion is substantially self-sustaining at room temperature i.e., so that the particles do not noticeably cream or settle out during normal storage (two weeks at 20° C.). Preferably the particles are of such size that at room temperature a 1% by weight dispersion of the antifoam ketone or in water possesses an opalescent haze which indicates that the particles are of colloidal dimensions and which exhibits the Tyndall effect. Dispersions of this extreme and very desirable particle size can be attained by passing the dispersion through a colloid mill or homogenizer, and this is specially advantageous when the dispersion medium is water.

Compared with many other known antifoam agents, the wax-like ketones and secondary alcohols referred to above are distinguished in addition to their excellent defoaming effect, by their chemical resistance to acid and alkaline liquids. Consequently, they can be used in processes and in compositions in which strong acids and alkalis are present. Advantageously, in these cases, the defoamers are dispersed in organic liquids which, under the given conditions, are not saponified or chemically changed in any way.

Owing to their excellent defoaming action and their chemical resistance, the defoaming compositions of the present invention can be used with suprisingly good results in a large number of industrial processes in which control or prevention of foam normally presents great difficulty. However, for use in particularly difficult or special instances it can be advantageous to add to the fluid antifoam dispersions other substances known to have a defoaming action such as fatty alcohols, esters of hydroxystearic acid and of hydroxystearic alcohol, alkylphenols, fatty acids, silicones, and the like.

The defoaming action which can be obtained with combinations of this type is frequently greater than that obtainable with any of the components.

According to the field of application, or to increase the stability or efficacy, the defoamer dispersions can contain additional and auxiliary agents which are customarily present in defoaming compositions for example thickeners such as aluminum, calcium or zinc stearate or finely divided silicic acid. The quantities of these additional constituents generally lie between 0.1% and 5% of the weight of the defoaming dispersion.

The defoaming dispersions can be added directly to the liquids which tend to form foam, such as the drilling and cutting oils used in the metalworking industry and polymer latex dispersions such as polyacrylate, polystyrene, polybutadiene and polyvinyl acetate dispersions. Accordingly, they can also be directly incorporated in aqueous papercoating compositions and oil based paints and dispersion paints (i.e., aqueous latex paints). A different possibility of use resides in adding the defoamer at place where the foam is formed, for example in the manufacture of paper and cellulose or the defoaming of waste water. In this case, the foam is suppressed or broken by sprinkling or spraying the defoamer in the working range of agitators or pumps, at the headbox of the papermaking machine, or at overflows and the like. The defoamers can also be used in the same manner to suppress troublesome foam in the food industry, for example in the production of sugar and yeast, in fermentation processes, etc.

The qualtities used depend upon the nature of the foaming liquid and its tendency to foam. Consequently, the amount of defoamer metered to the solution particularly by sprinkling or spraying, should be varied to obtain the amount of suppression desired. When the defoamers are added to foaming solutions or when they are incorporated in paint or in latices of film-forming polymers and the like, the quantities of defoamer required are approximately 0.5 g. to 10 g. per liter of the liquid being defoamed. A suitable amount can be readily found in any instance by trial.

The defoamers in accordance with the invention have proved to be particularly useful as additives to coolants and lubricants for cutting and non-cutting metalworking. To prevent corrosion, coolants and lubricants of this type usually contain, in addition to hydrocarbons and emulsifying constituents (soaps, sulfonates and the like) alkali constituents such as organic amines (for example diamines and polyamines, and aminoalcohols). The aqueous solutions or emulsions of these oil concentrates usually have pH values between 9 and 10.5. Auxiliary agents of this type have a considerable tendency to foam during use, and, for this reason, it is desirable to add foam inhibitors to these compositions as well.

Conventional foam inhibitors, such as pentaerythritol monostearate and hydroxystearyl monobehenate, lose their defoaming effect in these concentrates after long storage, at alkaline and acid pH values, since these defoamers are esters and are saponified by alkalis and acids.

The present invention will now be further described by means of the following examples. These examples are best embodiments of the invention and are not to be construed in limitation thereof.

FOAMING TESTS

Since drilling and cutting oil concentrates are diluted with water before use (they are aqueous emulsions), the antifoam properties of the dispersions of the present invention were determined as follows.

Into a 2-liter graduate is placed 500 ml. of a 2% solids drilling oil solution or emulsion produced by diluting the concentrate with distilled water. The solution or emulsion is circulated through the graduate by withdrawing the emulsion or solution from the bottom of the graduate through a glass tube attached to a laboratory hose pump and returning the liquid to the graduate through a second tube which terminates at the top of the graduate. The liquid is circulated at a speed of 4 liters per minute. A constant volume of foam forms in the graduate, the height of which depends on the composition of the liquid to be tested. The foam index of the liquid is given in terms of the height of the liquid in the graduate plus the volume of the foam. This is the control foam index.

The antifoam dispersions are tested in adding specified quantities of antifoam dispersion to the liquid and noting the change in the foam index of the solution under test as the liquid circulates.

Parts are by weight except when otherwise stated.

EXAMPLE 1

The following illustrates the production of an antifoaming composition of the present invention composed of a dispersion of particles of the defoaming agent in a hydrocarbon medium.

To 800 parts of mineral oil ($D_{15}$ = 0.889, $\eta$ 20 = 16 cST, solidification point = −49° C.) at 105° C. in an open vessel equipped with heater and agitator are added with agitation 160 parts of technical stearone followed by 20 parts by weight of aluminum stearate. After the two substances have dissolved completely the solution is slowly cooled to 70° C. with intensive agitation. 20 parts of a commercial silica pigment [Aerosil R 972® (Degussa)] are added at this temperature as thickener.

The mixture is now cooled rapidly to room temperature with continued intensive agitation.

EXAMPLE 2

The procedure of Example 1 is repeated except that technical behenone is used instead of the stearone. A similar product is obtained.

EXAMPLE 3

The procedure of Example 1 is repeated except that pentaerythrytol monostearate is used in place of the stearone. A similar product is obtained.

EXAMPLE 4

The following illustrates the defoaming properties of the compositions of Example 1, 2 and 3.

A drilling and cutting oil was prepared according to a commercial formulation from which the defoamer was omitted by making a mixture of the following.

| Name | % By Weight |
|---|---|
| Mineral oil | 80 |
| Petroleum sulfonate | 10 |
| Triethanolamine | 5 |
| Water | 5 |

To a sample of the resulting cutting oil was added 1% of the composition of Example 1. The procedure was repeated with addition of the composition of Example 2 and again with addition of the composition of Example 3.

These mixtures were emulsified with distilled water in the ratio to provide an emulsion containing 2% solids, and the foaming index of these emulsions were determined by the method described above. The foaming index was determined again in the same manner after 1, 3 and 6 months. Results were as follows.

FOAMING INDEX

| Age of Sample | Ml. of Foam After Minutes | | | | | | | |
|---|---|---|---|---|---|---|---|---|
| | 0.5 | 1 | 2 | 3 | 5 | 10 | 15 | 20 |
| Control | 1000 | 1260 | 1900 | 2000 | >2000 | >2000 | >2000 | >2000 |
| Example 1 Defoamer | | | | | | | | |
| Initial | 500 | 520 | 520 | 540 | 600 | 640 | 700 | 740 |
| 1 Month | 500 | 520 | 520 | 540 | 560 | 700 | 740 | 800 |
| 3 Months | 500 | 500 | 520 | 540 | 560 | 600 | 620 | 660 |
| 6 Months | 480 | 480 | 500 | 500 | 540 | 580 | 700 | 720 |
| Example 2 Defoamer | | | | | | | | |
| Initial | 500 | 500 | 500 | 500 | 500 | 500 | 520 | 520 |
| 1 Month | 500 | 500 | 500 | 500 | 500 | 560 | 640 | 680 |
| 3 Months | 500 | 500 | 500 | 500 | 500 | 500 | 500 | 500 |
| 6 Months | 480 | 480 | 500 | 500 | 500 | 500 | 520 | 520 |
| Example 3 Defoamer | | | | | | | | |
| Initial | 660 | 680 | 640 | 640 | 640 | 640 | 640 | 680 |
| 2 Months | 800 | 920 | 1180 | 1400 | 1680 | 1680 | 1800 | 2000 |
| 4 Months | 840 | 1000 | 1280 | 1640 | 1800 | 2000 | >2000 | >2000 |
| 9 Months | 860 | 1100 | 1380 | 1000 | 1800 | >2000 | >2000 | >2000 |

*Cutting oil only (no defoamer)

EXAMPLE 5

The defoamers in accordance with the invention can also be incorporated in latex paints. Latex paints comprise aqueous dispersions of synthetic film-forming polymers and suitable pigments. They also contain defoamers in addition to other additives. In order to obtain a non-porous coat when using latex paints, defoamer additives are required in order to prevent the formation of foam and to accelerate deaeration of the painted films. The latex paints are usually adjusted to an alkaline pH with ammonia. Accordingly, the defoamers used must be resistant to alkaline pH values for long periods of time.

MANUFACTURE OF ANTIFOAM DISPERSIONS

A number of antifoam dispersions were produced as follows.

To 895 parts of mineral oil ($D_{15}$ = 0.889, $\eta$ 20 = 16 cST, solidification point = −49° C.) heated to 105° C. in the apparatus of Example 1 were added 70 parts of one of the wax-like defoamers I–IV (below). After a solution had formed there were added 30 parts of the ester of a polyalkylene glycol (60% ethylene oxide, 40% propylene oxide, molar weight = 2,500) with stearic acid and 5 parts of aluminum stearate. A homogeneous solution formed which was rapidly cooled to room temperature with intensive agitation.

The wax-like defoamers were the following.
I Behenone (technical grade)
II Stearone (technical grade)
III Stearone (pure)
IV 18-Pentatriacontanol (hydrogenated stearone, acid number 1, carbonyl number 1, hydroxyl number 111, solidification point=80° C.)

EXAMPLE 6

The following illustrates alkaline latex paints of low foaming tendency as the result of the presence therein of defoaming agents according to the present invention.

A white gloss outside paint was produced in accordance with the following formula:

| Component | Parts by Weight |
| --- | --- |
| 1,2-Propylene glycol | 65.70 |
| Aqueous sodium polyacrylate solution, (25% by weight) | 14.00 |
| Anti-foaming agent | 0.95 |
| Water | 18.80 |
| Titanium dioxide pigment | 258.00 |
| Water | 47.00 |
| Fine particle size polyacrylate latex | 513.00 |
| Tributyl phosphate | 17.30 |
| Preservative | 2.80 |
| Anti-foaming agent (see below) | 0.95 |
| Ammonia | 1.90 |
| 1,2-Polypropylene glycol | 28.20 |
| Synthetic thickener | 9.40 |
| Water | 22.00 |
| Total (white gloss outside paint) | 1,000.00 |

The components were added in the sequence stated. The defoamers used were defoamer I–IV (above).

The foaming behavior of the foregoing paints was determined immediately after they had been produced.

In each instance, 80 parts of the paint were mixed with 20 parts of water and the mixture was agitated in a Dissolver (diameter of dispersion disc 40 mm.) for 1 minute at 2000 r.p.m. and 1 minute at 3000 r.p.m. 50 ml. of the product was immediately weighed out. The greater the weight of this volume of the sample, the lower is its air content and, accordingly, the better is the defoamer from the point of view of its defoaming properties.

The paints were further tested in an application test. The paint diluted with water in the ratio of 80:20 was agitated in a Dissolver for 1 minute at 2000 r.p.m. The sample was then applied to a carefully cleaned glass plate by means of a lambskin roller. The coat of paint is visually assessed after drying for the number of air bubbles. A rating of 1 indicates that the plate had a very large number of flaws caused by air bubbles. The rating of 6 indicates that the coating of paint dried completely without air pockets or pinholes. Intermediate rating indicate an intermediate number of air pockets or pinholes.

The following results were obtained in the test with the defoamers I–IV.

| Defoamer | Weight of 50 Ml. (grams) | Pinhole Rating |
| --- | --- | --- |
| Control (no defoamer) | 38.7 | 1 |
| I | 55.8 | 4 |
| II | 54.6 | 4 |
| III | 49.8 | 3–4 |
| IV | 50.6 | 3–4 |

The results show that defoamer I gives best results.

EXAMPLE 7

Alkaline cleaning agents containing water glass and phosphates in addition to caustic soda are frequently used for the industrial cleaning of glasses and bottles. Although these mixtures scarcely foam themselves, foam-inhibiting agents have to be added to them.

Residues of adhesives originating from the labels, components of the printing ink and residues of the contents of the bottles (lemonade, milk, beer and the like) readily lead to the formation of foam when formation of foam is not prevented by antifoam additives, particularly in automatic bottle-cleaning plants.

The defoamer is added to the cleaning agent during the mixing of the components and, if required, can be sprayed in order to obtain a suitable uniformity of distribution.

An effective bottle-cleaning agent containing a defoamer of the present invention was produced by intensively mixing the following materials.

| Component | % By weight |
| --- | --- |
| Caustic soda | 75 |
| Sodium triphosphate ($Na_5P_3O_{10}$) | 6 |
| Sodium metasilicate ($Na_2SiO_3 \cdot 5 H_2O$) | 15.5 |
| Defoamer (Example 1) | 3.5 |

A 1.5% by weight solution of a typical alkaline cleaning agent was produced to determine the effectiveness of the anti-foaming agent. To one portion of this was added (a) 0.075% of alkylbenzene sulfonate and to a second portion was added (b) 0.1% of potassium oleate as wetting agents based on the weight of the solution. The foaming tendency of the mixtures was determined at 60° C. in the apparatus described above.

The following quantities of foam (including 500 ml. of liquid) were observed in the test apparatus in each test after 1 minute:

| Wetting Agent | Without Defoamer | With Defoamer |
| --- | --- | --- |
| (a) | 2000 ml. | 680 ml. |
| (b) | 2000 ml. | 760 ml. |

The foam-inhibiting effect of the defoamer is not impaired during prolonged storage of cleaning agent at an alkaline pH.

We claim:

1. A dispersion useful as a foam suppressant, wherein the continuous phase is an organic liquid having a solidification point below 5° C. and a boiling point above 80° C. and wherein the dispersed phase comprises at least 1% based on the weight of said dispersion of a higher aliphatic component selected from the group consisting of the $C_{22-70}$ aliphatic ketones, $C_{22-70}$ aliphatic secondary alcohols, and mixtures thereof, said continuous phase being substantially a non-solvent for said aliphatic component; the size of the particles of said dispersed phase being such that the dispersion does not separate on standing for two weeks at 20° C.; the amount of said dispersed phase being such that said dispersion is fluid at 40° C.

2. A dispersion according to claim 1 wherein the aliphatic component has a chain length of 23-43 carbon atoms.

3. A dispersion according to claim 1 wherein said ketones and alcohols are alkanones and alkanols.

4. A dispersion according to claim 1 wherein the particle size of the aliphatic component is such that the dispersion exhibits the Tyndall effect when viewed by transmitted light.

5. A dispersion according to claim 1 wherein the continuous phase thereof is mineral oil.

6. A dispersion according to claim 1 wherein the weight of the aliphatic component is 5% to 15% of the total weight of said dispersion.

7. A dispersion according to claim 1 containing an effective amount of a substance known to have a defoaming action as fortifying agent for said dispersion.

8. A dispersion according to claim 1 containing a water-insoluble polyvalent metal soap as thickener.

9. A dispersion according to claim 8 wherein the soap is aluminum stearate.

10. A dispersion according to claim 1 wherein said aliphatic component contains 22 to 50 carbon atoms.

11. A dispersion according to claim 1 wherein said aliphatic component is 12-tricosanone.

12. A dispersion according to claim 1 wherein said aliphatic component is 16-hentriacontanone.

13. A dispersion according to claim 1 wherein said aliphatic component is 18-pentatriacontanone.

14. A dispersion according to claim 1 wherein said aliphatic component is behenone.

15. A dispersion according to claim 1 wherein said aliphatic component is 12-tricosanol.

16. A dispersion according to claim 1 wherein said aliphatic component is 16-hentriacontanol.

17. A dispersion according to claim 1 wherein said aliphatic component is 18-pentatriacontanol.

18. A dispersion according to claim 1 wherein said aliphatic component is a 50% by weight mixture of said ketone and said alcohol.

19. A method of decreasing the tendency of a liquid to form foam when agitated with inclusion of air, which comprises adding to said liquid a small but effective amount therefor of a dispersion according to claim 1.

20. A method according to claim 19 wherein said liquid is a latex paint.

21. A dispersion useful as a foam suppressant, wherein the continuous phase is water and wherein the dispersed phase comprises at least 1% based on the weight of said dispersion of a higher aliphatic component selected from the group consisting of $C_{22-70}$ aliphatic secondary alcohols, and mixtures of $C_{22-70}$ aliphatic secondary alcohols and of $C_{22-70}$ aliphatic ketones, said continuous phase being substantially a non-solvent for said aliphatic component; the size of the particles of said dispersed phase being such that the dispersion does not separate on standing for two weeks at 20° C.; the amount of said dispersed phase being such that said dispersion is fluid at 40° C.

22. A dispersion according to claim 21 wherein the aliphatic component has a chain length of 23-43 carbon atoms.

23. A dispersion according to claim 21 wherein said ketones and alcohols are alkanones and alkanols.

24. A dispersion according to claim 21 wherein the particle size of the aliphatic component is such that the dispersion exhibits the Tyndall effect when viewed by transmitted light.

25. A dispersion according to claim 21 wherein the weight of the aliphatic component is 5% to 15% of the total weight of said dispersion.

26. A dispersion according to claim 21 containing an effective amount of a substance known to have a defoaming action as fortifying agent for said dispersion.

27. A dispersion according to claim 21 containing a water-insoluble polyvalent metal soap as thickener.

28. A dispersion according to claim 21 wherein the soap is aluminum stearate.

29. A dispersion according to claim 21 wherein said aliphatic component contains 22 to 50 carbon atoms.

30. A dispersion according to claim 21 wherein said aliphatic component is 12-tricosanol.

31. A dispersion according to claim 21 wherein said aliphatic component is 16-hentriacontanol.

32. A dispersion according to claim 21 wherein said aliphatic component is 18-pentatriacontanol.

33. A dispersion according to claim 21 wherein said aliphatic component is a 50% by weight mixture of said ketone and said alcohol.

34. A method of decreasing the tendency of a liquid to form foam when agitated with inclusion of air, which comprises adding to said liquid a small but effective amount therefor of a dispersion according to claim 21.

35. A method according to claim 34 wherein said liquid is a latex paint.

36. A latex paint which contains a small but effective amount as anti-foam agent of a dispersion, wherein the continuous phase is a liquid having s solidification point below 5° C. and a boiling point above 80° C. and wherein the dispersed phase comprises at least 1% based on the weight of said dispersion of a higher aliphatic component selected from the group consisting of the $C_{22-70}$ aliphatic ketones, $C_{22-70}$ aliphatic secondary alcohols, and mixtures thereof, said continuous phase being substantially a non-solvent for said aliphatic component; the size of the particles of said dispersed phase being such that the dispersion does not separate on standing for two weeks at 20° C.; the amount of said dispersed phase being such that said dispersion is fluid at 40° C.

* * * * *